(12) United States Patent
Nord et al.

(10) Patent No.: US 10,363,437 B2
(45) Date of Patent: Jul. 30, 2019

(54) REAL TIME TREATMENT PARAMETER ALGORITHM FOR MOVING TARGETS

(75) Inventors: Janne Nord, Espoo (FI); Sami Siljamaki, Helsinki (FI)

(73) Assignee: Varian Medical Systems International AG (CH)

( * ) Notice: Subject to any disclaimer, the term of this patent is extended or adjusted under 35 U.S.C. 154(b) by 0 days.

(21) Appl. No.: 12/332,739

(22) Filed: Dec. 11, 2008

(65) Prior Publication Data
US 2010/0150309 A1 Jun. 17, 2010

(51) Int. Cl.
*A61B 6/00* (2006.01)
*A61N 5/10* (2006.01)

(52) U.S. Cl.
CPC ......... *A61N 5/1049* (2013.01); *A61N 5/1038* (2013.01); *A61N 5/1064* (2013.01); *A61N 5/1071* (2013.01); *A61B 6/486* (2013.01); *A61N 2005/1072* (2013.01)

(58) Field of Classification Search
CPC ........ A61N 5/10; A61N 5/103; A61N 5/1031; A61N 5/1036–1038; A61N 5/1045; A61N 5/1048; A61N 5/1064; A61N 5/1065; A61N 5/1067; A61N 5/1071; A61N 2005/1072; A61B 6/486; A61B 6/50
USPC ........... 378/62–65, 68, 69, 95, 97, 108, 165; 600/407, 410, 411, 415–417, 425–429, 600/436, 484, 529, 531–543
See application file for complete search history.

(56) References Cited

U.S. PATENT DOCUMENTS

| 2004/0165696 | A1 | 8/2004 | Lee |
| 2006/0074292 | A1* | 4/2006 | Thomson et al. ............ 600/411 |
| 2007/0041494 | A1* | 2/2007 | Ruchala et al. ................ 378/65 |
| 2007/0041495 | A1* | 2/2007 | Olivera et al. ................. 378/65 |
| 2007/0041497 | A1* | 2/2007 | Schnarr et al. ................ 378/65 |
| 2007/0043286 | A1* | 2/2007 | Lu et al. ...................... 600/407 |
| 2007/0055142 | A1* | 3/2007 | Webler ......................... 600/425 |

(Continued)

FOREIGN PATENT DOCUMENTS

| WO | 1997042522 A1 | 4/2007 |
| WO | 2007045075 A1 | 4/2007 |

(Continued)

OTHER PUBLICATIONS

International Search Report and Written Opinion dated Apr. 14, 2010 for PCT/IB2009/007714.

(Continued)

*Primary Examiner* — Anastasia Midkiff
(74) *Attorney, Agent, or Firm* — Vista IP Law Group, LLP

(57) ABSTRACT

A method of determining a treatment parameter, includes determining an accumulated dose at a target region that undergoes motion, determining an accumulated dose at a critical region, and determining the treatment parameter based on the determined accumulated dose at the target region and the determined accumulated dose at the critical region, wherein the act of determining the treatment parameter is performed during a treatment session. A method of determining a treatment parameter, includes tracking a position of a target, delivering radiation to the target based on the tracked position, and compensating for an inaccuracy of the tracked position by using information regarding a delivered dose to determine a treatment parameter for a next beam delivery.

30 Claims, 6 Drawing Sheets

(56) References Cited

U.S. PATENT DOCUMENTS

| | | | |
|---|---|---|---|
| 2008/0002811 | A1 | 1/2008 | Allison |
| 2008/0011945 | A1* | 1/2008 | Maurer et al. ............. 250/252.1 |
| 2008/0031404 | A1* | 2/2008 | Khamene et al. ................ 378/6 |
| 2008/0159478 | A1* | 7/2008 | Keall ................... A61N 5/1042 378/65 |
| 2008/0212737 | A1* | 9/2008 | D'Souza .............. A61N 5/1049 378/65 |
| 2008/0281192 | A1* | 11/2008 | Keall et al. ................... 600/426 |
| 2009/0161827 | A1 | 6/2009 | Gertner et al. |
| 2010/0036378 | A1* | 2/2010 | Savery et al. ................. 606/42 |

FOREIGN PATENT DOCUMENTS

| | | |
|---|---|---|
| WO | 2008005129 A2 | 1/2008 |
| WO | 2009055801 A2 | 4/2009 |

OTHER PUBLICATIONS

International Search Report and Written Opinion dated Jun. 23, 2011 for PCT/IB2009/007714.
Supplementary European Search Report dated May 4, 2012, for EP Patent Application No. 09 831534.4.
First European Office Action dated Feb. 11, 2013 , for EP Patent Application No. 09 831534.4.
Examination Report dated Oct. 9, 2014, for related European Patent Application No. 09831534.4, 5 pages.
Summons to attend oral proceedings pursuant to Rule 115(1) EPC dated May 3, 2016 for corresponding EP Patent Application No. 09831534.4, 3 pages.
Communication pursuant to Article 94(3) EPC dated Mar. 23, 2015, for corresponding European Patent Application No. 09 831 534.4, 6 pages.

* cited by examiner

REAL TIME TREATMENT PARAMETER ALGORITHM FOR MOVING TARGETS

FIELD

This application relates generally to radiation therapy, and more specifically, to systems and methods for determining treatment parameter(s) for radiation therapy.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. Such treatment plan may be determined during a radiation planning session before a treatment session in which treatment radiation is actually delivered to a patient. The goal of the treatment planning is to determine and prescribe a desired dose of radiation to be delivered to a patient.

In radiation therapy, it is important to deliver a desired amount of dose to target, such as a tumor tissue, while minimizing dose to critical organs that contains healthy tissues. Often radiation rays pass through both critical structures and targets during treatment. Intensity modulated radiation therapy (IMRT) uses ray intensities that have been optimized so that homogeneous dose is prescribed to targets while trying to maintain critical organs' dose within acceptable limits. Sometimes if the target moves (for example due to breathing), the intensity rays can be moved according to the target motion to thereby track the target. By tracking the target, the resulting dose in target may have a higher chance of coming out as planned.

However, existing tracking techniques may not provide an accurate tracking of the target. For example, in tracking techniques that predict the position of the target, the actual position of the target may be different from the predicted position. As a result, the delivered beam may not hit the target accurately, and the target may not receive the desired dose as planned.

Also, in some cases, critical organs may not move, or they may move differently from that of the target. In such cases, as the beam is moved to track the target, the resulting intensity rays may move relative to critical organs, and may unintentionally traverse the critical organs, thereby resulting in the critical organs dose that is beyond an acceptable limit. In addition, an inaccuracy of the tracked target position as described above may also cause the critical organs to receive higher dose than planned.

SUMMARY

In accordance with some embodiments, a method for tracking target(s) while ensuring that critical organs doses stay within acceptable limits is provided. In the method, at least two fluences are used. The first fluence limits the critical organ dose, and the second fluence maintains target dose homogeneity. The method tracks the target, and accumulates fluences to target and critical organs separately. Then the method produces leaf sequence in real time so that target fluence will be realized while limiting fluence to critical organs. Real time leaf sequencing algorithm generates a leaf sequence for radiation in the next time interval to be delivered. Target movement is predicted for this time interval. Leaf sequencer produces a sequence that increases the accumulated target fluence where planned target fluence level has not been achieved if the critical organ fluence level is below the allowed limit.

In accordance with some embodiments, a method of determining a treatment parameter, includes determining an accumulated dose at a target region that undergoes motion, determining an accumulated dose at a critical region, and determining the treatment parameter based on the determined accumulated dose at the target region and the determined accumulated dose at the critical region, wherein the act of determining the treatment parameter is performed during a treatment session.

In accordance with other embodiments, a system for determining a treatment parameter includes a processor, wherein the processor is configured for determining an accumulated dose at a target region that undergoes motion, determining an accumulated dose at a critical region, and determining the treatment parameter during a treatment session based on the determined accumulated dose at the target region and the determined accumulated dose at the critical region.

In accordance with other embodiments, a method of determining a treatment parameter, includes tracking a position of a target, delivering radiation to the target based on the tracked position, and compensating for an inaccuracy of the tracked position by using information regarding a delivered dose to determine a treatment parameter for a next beam delivery.

In accordance with other embodiments, a system for determining a treatment parameter includes a processor, wherein the processor is configured for tracking a position of a target, generating a control signal for delivering radiation to the target based on the tracked position, and compensating for an inaccuracy of the tracked position by using information regarding a delivered dose to determine a treatment parameter for a next beam delivery.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
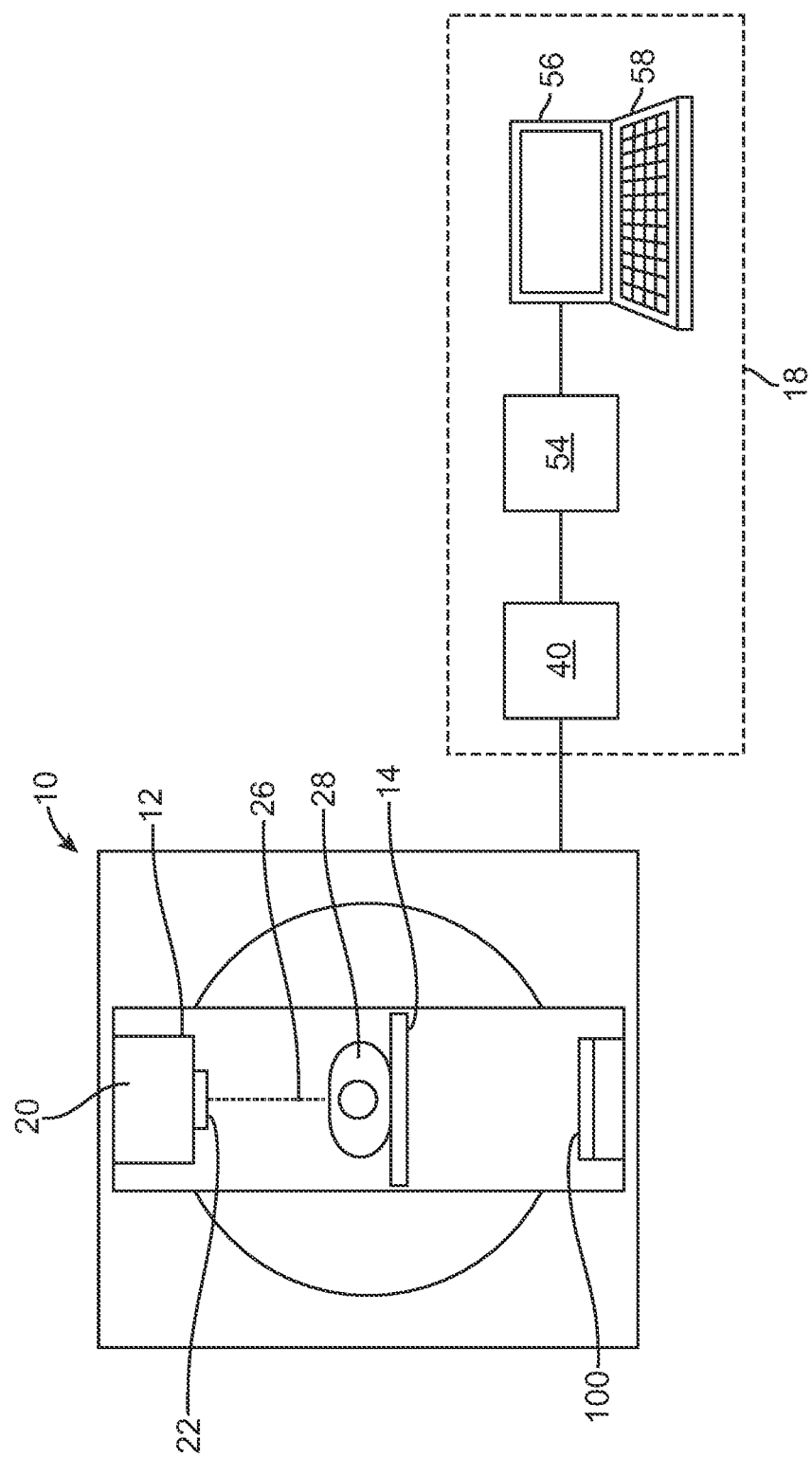
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the system 10 has a ring gantry, in which cases, the radiation source 20 is directly mounted to the gantry, and the system 10 does not include the arm-configuration described above. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
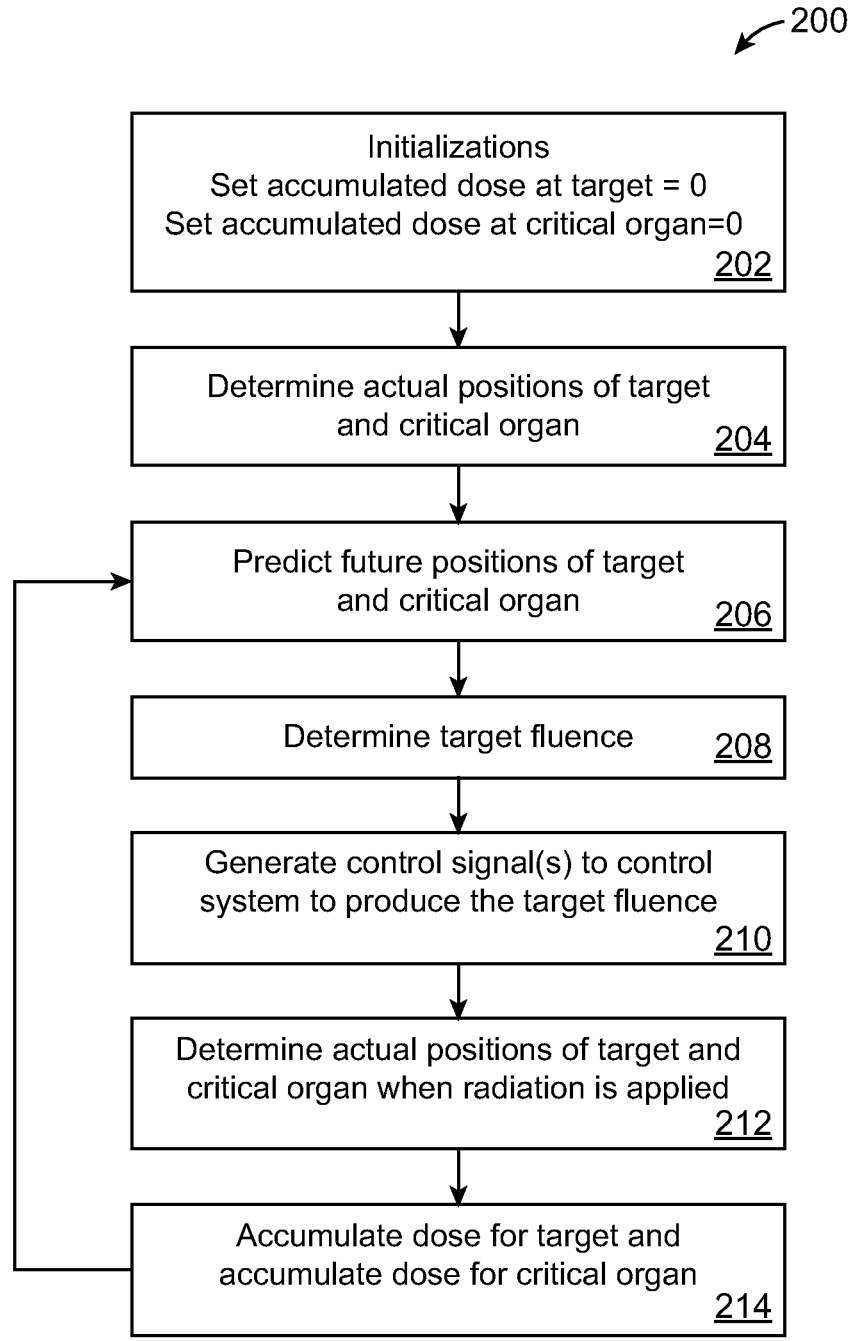
FIG. 2 illustrates a method of determining a treatment plan in accordance with some embodiments.
Figure 3:
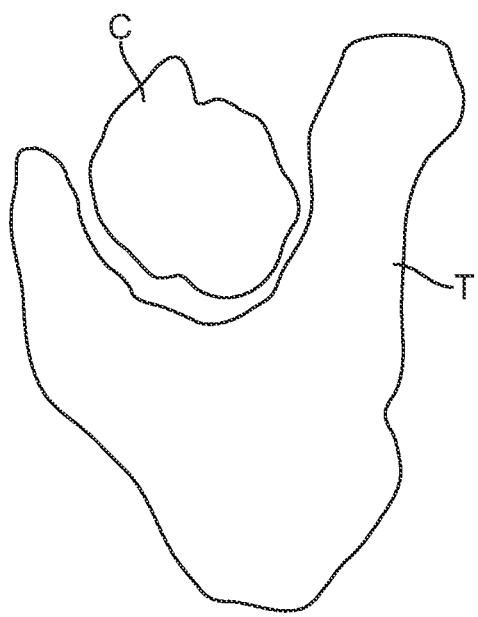
FIG. 3 illustrates an example of a target next to critical tissue.

FIG. 2 illustrates a method 200 for determining a radiation treatment plan in real time that may be used by the system 10 in accordance with some embodiments. As used in this specification, the term "treatment plan" may refer to any information that can be used directly or indirectly to prescribe a treatment. For example, in some embodiments, the treatment plan may include one or more treatment parameters, wherein a treatment parameter may represent one or more of a target fluence, a dose, a dose rate, a gantry position, a gantry speed, a leaf sequence, a collimator position, a beam energy, a beam-on condition, a beam-off condition, and a patient support position. The method 200 will be described with reference to delivering radiation using the system 10 of FIG. 1 to treat a target or target region T that is adjacent to critical region C (FIG. 3). In the illustrated example, it is assumed that the target T is a lung tumor. In other embodiments, the method 200 is also applicable for delivering radiation to target(s) other than the lung, and/or to target(s) having different configuration as that shown in the figure.

Before a treatment session begins, a preliminary treatment plan is determined in which the critical organ dose and target dose are optimized based on assumed position and movement of the patient. In some cases, the actual movement may be different from planned movement. Embodiments of the method 200 described herein account for these differences between planning and actual movements, and the differences in dose resulted therefrom, in real time. In the illustrated example, a number of fields for IMRT treatment (e.g., as in arc treatment) have been planned. For each field in the preliminary treatment plan, an optimal fluence map for target and a maximum fluence map for critical organs are determined. The preliminary treatment plan may then be saved for later use, such as for use during a treatment session. In some embodiments, the preliminary treatment plan may be determined right before (e.g., in the same day) the treatment session is performed. In other embodiments, the preliminary treatment planning and the actual treatment may be performed in different days.

During a treatment session, for each field (direction), the system 10 is first set to correct configuration (e.g., gantry rotated to correct direction). The method 200 is then performed for each field, as follows.

First, the actual accumulated dose or fluence $AD_T$ delivered to the target T is set to zero, and the actual accumulated dose or fluence $AD_C$ delivered to the critical organ C is set to zero (Step 202). Such may be accomplished by the processor 54 initializing variables $AD_T$ and $AD_C$ to have zero values.

Next, the actual position of the target T and the actual position of the critical organ C are determined (Step 204). Any techniques for determining position of an interested part that are known in the art may be used to accomplish such objective. In some embodiments, the target and critical organ positions are estimated based on available tracking technology. There are several alternatives. In some embodiments, real time imaging of actual target and/or critical organs may be used to obtain images of the target and critical organ. The images may then be used to determine the positions of the target and the critical organ based on known localization techniques. In other embodiments, the processor may be configured to perform image registration, in which the positions of the target and the critical organ are determined by matching the image with a reference image for which the positions of the target and the critical organ are known. In other embodiments, external/internal markers whose position correlates with target and/or critical organ movements based on a predetermined model may be used. Sometimes movement of tumor in the lung may correlate well with external marker(s), and so if the position of the external marker(s) is known, then the position of the target T can be determined. In some cases only target or critical organ moves while the other is static. For example in lung, the tumor may be mobile while spine is static. In this case, external marker(s) may be used to measure breathing phase that may correlate well with target position. Target position is then determined based on a predefined model in which the spine is assumed to be static. Other methods for determining the positions of the target and the critical organ may be used in other embodiments.

Figure 4:
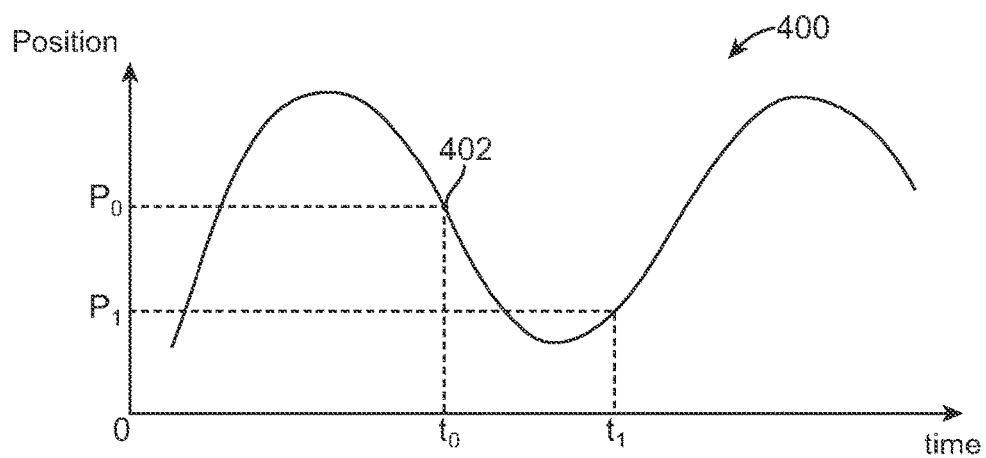
FIG. 4 illustrates a breathing graph having positional points.

Next, the processor 54 predicts a future position of the target T and a future position of the critical organ C (Step 206). In particular, the positions of the target T and the critical organ C at a certain prescribed future time may be predicted by the processor 54. For example, the prescribed time may be 0.4 second from the current time, at which a treatment is to be executed, such as to apply a determined leaf sequence. In some embodiments, the positions of the target T may be predicted by using a position monitoring system. For example, in the case of breathing movement, the system 10 can include a breathing-monitoring system (e.g., a camera with a marker block) to determine a position of the patient, and predict a phase of a breathing cycle based on the determined position. In such breathing-monitoring system, the marker block with a plurality of markers is coupled to the patient, and a camera is then used to view the marker block. As the patient breathes, the marker block moves up and down correspondingly with the breathing, and the sensed images by the camera are processed by the processor to determine the positions of the marker block, which represent the positions of the patient due to breathing. FIG. 4 illustrates a breathing graph 400 representing a breathing pattern of the patient, which may be generated by plotting the positional points of the marker block/patient. In some embodiments, such breathing pattern 400 may be recorded previously. During the method 200, the tracked current position at t0, represented by point 402, may be compared with the previously recorded breathing pattern 400, and the breathing pattern 400 is then used to predict the position at a future time t1. In the illustrated example, the current position at time t0 is P0, and the predicted position at future time t1 is P1. In some embodiments, pattern matching may be performed to compare the current wave form that includes positional point 402 with the previously recorded pattern to determine where the current point 402 is compared to the reference pattern. The wave form may include a plurality of positional data (e.g., positional data within the last 0.5 second) that are part of the current set of breathing pattern including the current point 402.

Figure 5:
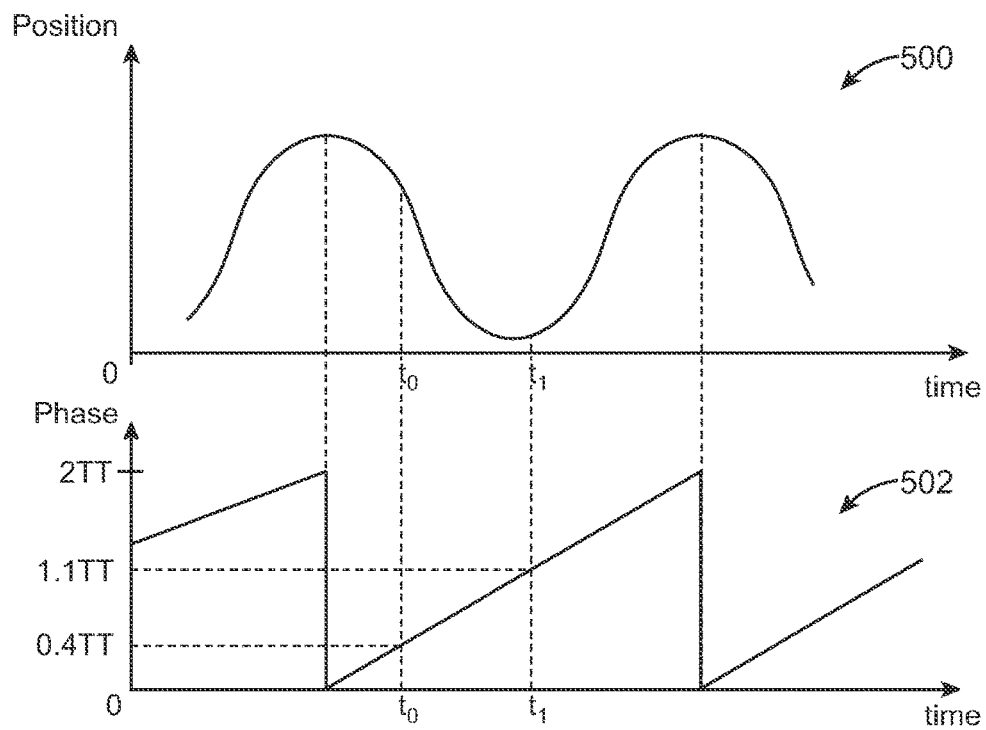
FIG. 5 illustrates a breathing graph together with a corresponding phase graph.

In other embodiments, the determined position may be used to determine a corresponding phase of a breathing cycle, wherein the phase represents a degree of completeness of the breathing cycle. FIG. 5 illustrates a breathing graph 500, which may be converted into a phase graph 502. In the illustrated embodiments, the phase range of the breathing cycle may be between 0 to $2\pi$, with the 0 and $2\pi$ values representing the peak of the respiratory cycle. In some cases, the determined current position may be used to determine the corresponding phase (e.g., $\pi$ value at t0), and the system can then predict a future phase at a certain future time (e.g., t1). In the illustrated example, the current time t0 is $0.4\pi$, and the predicted phase at t1 is $1.1\pi$.

Systems and methods for predicting a breathing phase and/or position are well known in the art, and will not be described in further detail. For example, systems and methods for predicting a breathing phase have been described in U.S. Pat. No. 6,959,266, the entire disclosure is incorporated by reference herein.

In the illustrated embodiments, the predicted breathing position of the patient or the predicted phase may be used to determine the predicted positions of the target T and the critical region C. For example, in some embodiments, each positional point/phase value associated with the patient's breathing may correspond with a position of the target T and/or the critical region C. In such cases, by knowing the positional point/phase of the patient's breathing, the corresponding position of the target T and/or the critical region C can then be determined.

Figure 6:
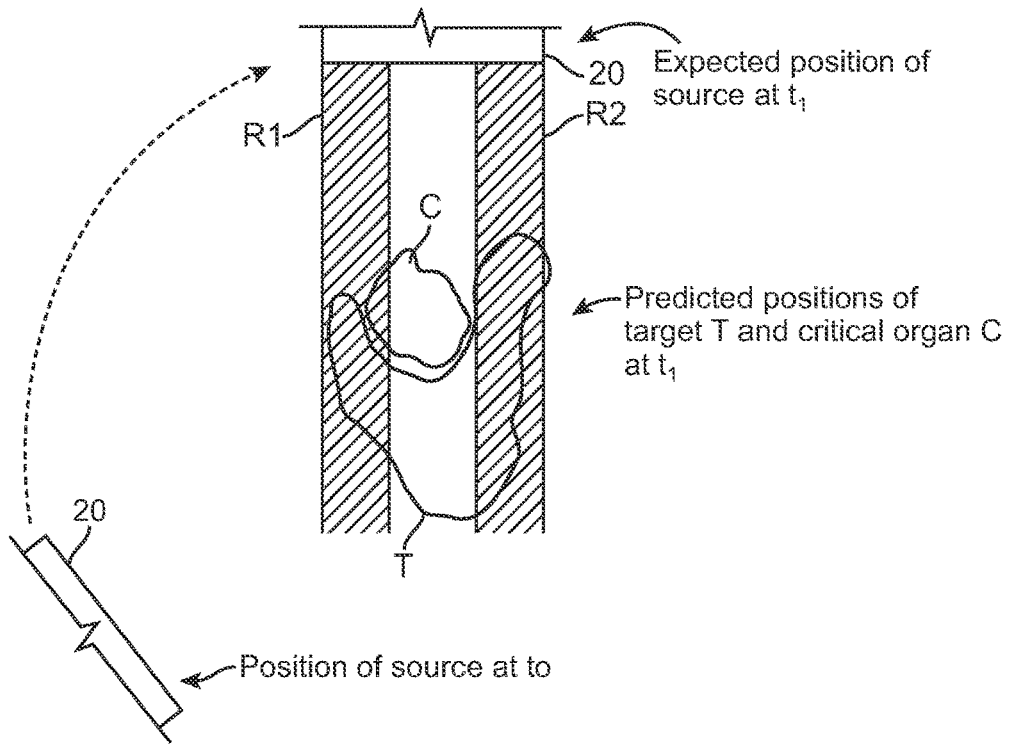
FIG. 6 illustrates graphically an example of a treatment plan.

Returning to FIG. 2, next, using the predicted positions of the target T and/or the critical region C, the processor 54 determines a target fluence (fluence desired to be applied) so that when radiation is delivered at the future time (1) the accumulated dose for the critical organ C is less than a prescribed threshold, and (2) at least some of the undelivered dose is delivered to the target T (Step 208). The prescribed dose threshold for the critical organ C is selected such that the accumulated dose for the critical organ C will not exceed a value that becomes harmful for, or may otherwise injure, the critical organ C. In some embodiments, the prescribed dose threshold for the critical organ C may be inputted by a user to the processor 54. In the illustrated embodiments, the target fluence is determined such that as much of the undelivered dose is delivered to the target T as possible. In some cases, the dose (or fluence) for the target T should be as close to that prescribed as possible (e.g., not less but also not more). In other cases, the dose in target T is allowed to be higher than planned. FIG. 6 illustrates the concept of step 208. As shown in the figure, the processor 54 at time t0 predicts the positions of the target T and critical region C at future time t1 to be that as shown graphically. Also, at the future time t1, the radiation source 20 will be at the position shown in the figure. In the illustrated example, based on the predicted positions of the target T and the critical region C, the processor 54 determines the target fluence that includes a first portion R1 and a second portion R2, and no fluence therebetween (e.g., a target fluence of 1111000111), such that radiation is prescribed to be delivered to the portions of the target T on either side of the critical organ C, and no radiation is prescribed to be delivered to the critical organ C.

In some embodiments, the determined target fluence is translated into machine parameters, which can be used by the processor 54 to control an operation of the system 10. For example, in some cases, the determined target fluence may be translated into a leaf sequence such that a desired beam profile for the fluence can be created. Such may be accomplished by the processor 54 performing a leaf sequence optimization in real time. In other embodiments, instead of, or in addition to a leaf sequence, the determined target fluence may be translated into other machine parameters, such as gantry angle, gantry rotational speed, beam energy, beam-on, beam-off, radiation source angle(s), dose rate, and/or patient support's 14 position.

In the illustrated embodiments, the target fluence is determined in real time, and the translation of the target fluence into machine parameter(s) is also performed in real time. As used in this specification, the term "real time" may refer to the act (e.g., determining target fluence, or translating to machine parameter(s), etc.) being performed during a treatment procedure. In other embodiments, the term "real time" may refer to the act being performed within a short period, such as, within 5 seconds, and more preferably, within 2 seconds, after the actual position of the target T and/or the actual position of the critical organ C has been determined, e.g., as in step 204.

Next, the system 10 is operated to attempt to produce the target fluence determined in step 208 when the prescribed future time is reached (Step 210). For example, the processor 54 may generate one or more control signals to cause the gantry to rotate, cause the gantry to stop rotating, cause the gantry to accelerate, cause the gantry to decelerate, stop a radiation beam 26, change an energy of the radiation beam 26, operate the collimator 22 (e.g., adapt a leaf sequence by moving one or more leaves), or any combination of the foregoing. In other embodiments, instead of, or in addition to any of the above combination, if the radiation source 20 is rotatable, e.g., about one or more axes, the processor 54 may also generate one or more control signals to cause the radiation source 20 to rotate about one or more axes. In further embodiments, instead of, or in addition to any of the above combination, the processor 54 may also position the patient support 14, e.g., translate along one or more axes and/or rotate about one or more axes, to thereby produce the target fluence. When the desired machine configuration (gantry position, leaf sequence, etc.) has been achieved, radiation is then delivered using the radiation source 20 to create the target fluence.

Figure 7:
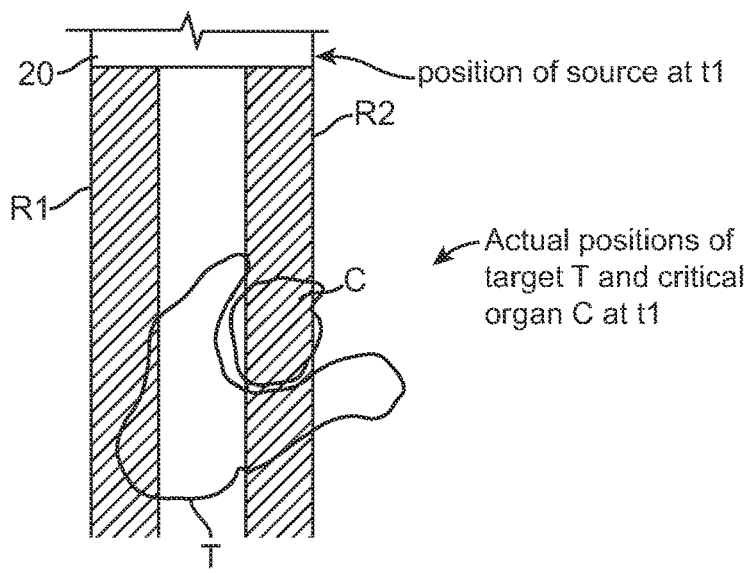
FIG. 7 illustrates graphically an example of an actual execution of a treatment plan.

In some embodiments, when performing step 210, the processor 54 is configured to operate the system to produce the target fluence as accurately as possible. However, because the actual positions of the target T and the critical organ C may be different from the predicted positions, and in some cases, also due to machine limitations (e.g., gantry cannot be rotated fast enough or above a prescribed safety speed), the created fluence may not be completely accurate. FIG. 7 illustrates such a concept. As shown in the figure, the actual position of the target T and the actual position of the critical organ C at t1 are different from the respective predicted positions (illustrated in FIG. 6), which were predicted at t0. As a result, when the system 10 creates the fluence at t1, some of the radiation R2 that was intended for only a region of the target T is actually delivered to the critical organ C.

In the illustrated embodiments, the actual position of the target T and the actual position of the critical organ C at time t1 when the treatment is executed in step 210 are determined (Step 212). Such may be accomplished by detecting marker position, and correlating the marker position with positions of the target T and the critical organ C. In other embodiments, the actual position of the target T and the actual position of the critical organ C when radiation is being delivered in step 210 may be determined by obtaining an image of the target T and the critical organ C. For example, an x-ray image, CT image, or any of other types of images may be obtained to thereby determine the actual positions of the target T and the critical region C.

The processor 54 next determines the actual accumulated dose for the target T, and the actual accumulated dose for the critical organ C based on the actual position of the target T and the critical organ C (Step 214). Various techniques may be used to determine the actual accumulated doses for the target T and critical organ C. In the illustrated embodiments, since the actual positions of the target T and the critical organ C are known, and the actual position of the radiation source 20 when radiation was delivered in step 210 is also known, the processor 54 can then determine the amount of radiation (dose) delivered in step 210 to different parts of the target T and the critical organ C. The determined actual dose (resulted from step 210) delivered to the target T is then accumulated with previously delivered dose (if any) at the target T. Similarly, the determined actual dose (resulted from step 210) delivered to the critical organ C is also accumulated with previously delivered dose (if any) at the critical organ C. In some cases, the accumulated dose may be accumulated fluence for each direction. In this case, the actual two dimensional fluence is mapped to critical organ and target. The actual delivered radiation fluence is summed to the already delivered fluence to the actual measured position in both critical organ and target. In further embodiments, the accumulated doses at the target T and critical organ C may be determined by taking a high energy image, and obtaining dose info from the image. Such may be accomplished by using the same radiation source 20 (if it is capable of providing an imaging beam with a suitable energy for imaging) or a different radiation source.

The processor 54 then repeats steps 206-214 to determine additional target fluences, continue controlling the system 10 to achieve the determined target fluences, and determine actual accumulated doses for the target T and critical organ C, respectively. When the processor 54 repeats step 208 of determining a target fluence, the actual accumulated dose of the target T and the actual accumulated dose at the critical organ C that are resulted from previously applied radiation are taken into account. For example, following the above example, because of the error in the predicted positions of the target T and the critical organ C, the accumulated dose to the critical organ C is higher than expected, as discussed. So in step 208, the processor 54 may be configured to determine the next target fluence so that less dose is provided to the critical organ C. Similarly, in other embodiments, if an error in the tracking position of the target T results in less accumulated dose to the target T than expected, in step 208, the processor 54 may be configured to determine the next target fluence so that more radiation dose is provided to the target T. In further embodiments, if extra dose is delivered to some region due to tracking error, the extra dose may be removed from the dose to be delivered during later treatment.

In some embodiments, the steps are repeated until the target T receives all of the prescribed radiation dose—e.g., until the accumulated dose at the target T reaches a prescribed dose requirement. In other embodiments, the steps are repeated until the accumulated dose at the target organ C exceeds a certain prescribed threshold. In some embodiments, the processor 54 is configured to track both the accumulated dose of the target T and the accumulated dose of the critical organ C, and will stop the radiation application when either the condition that the accumulated dose at the target T reaches a desired value, or the condition that the accumulated dose at the critical organ C is above a safety level, is met.

As illustrated in the above embodiments, because the determination of target fluence in step 208 takes into consideration of the actual cumulated dose that has been delivered to the target T and the actual cumulated dose that has been delivered to the critical organ C, any inaccuracy of radiation application (e.g., too much radiation to critical organ C and/or not enough radiation to target T) due to tracking error is automatically compensated for—i.e., by including the tracking error contribution in the next optimization round. Thus, the method 200 is advantageous because it can reduce the effect (e.g., the effect of too much radiation to critical organ C, and/or not enough radiation to target T) of tracking error. Also, the above technique is advantageous in that the preliminary treatment plan does not need to be complete or very detailed since most of the treatment parameters may be determined in real time during the treatment session.

Although the above embodiments have been described with reference to delivering treatment radiation that is in the form of x-rays, in other embodiments, the system and technique described herein may be used for other types of treatment energy. For examples, in other embodiments, the radiation source 20 may be a proton source for delivering protons to treat a patient, or an electron source for delivering electrons. Accordingly, embodiments of the technique described herein may be used to determine treatment parameter for other types of treatment, such as proton treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

In the above embodiments, the method 200 has been described as being performed by the processor 54. In other embodiments, instead of or in addition to the processor 54, at least part of the method 200 may be performed by one or more other processor(s). As used in this specification, the term "processor" is not limited to a single processing unit, and may refer to one or more processing units.

In the above examples, only one target T and one critical organ C are illustrated. In other embodiments, the method 200 can determine more than one accumulated fluences for a plurality of targets T, and/or more than one accumulated fluences for a plurality of critical regions C. In some cases, every object that moves differently can have its own fluence. For example two targets T1, T2 that move differently could have their own respective accumulated fluences. The targets may be different parts of a same target region, or may be different regions that are separate from each other. In some embodiments, to increase an accuracy of the tracking, and/or to increase the radiation distribution tracking of a target region, a target region may be divided into a plurality of targets, which each target having its own accumulated fluence. Also, different critical organs or tissue regions can have different respective accumulated fluences. For example, a first part of a critical region may have a first accumulated fluence, and a second part of the critical region may have a second accumulated fluence that is different from the first accumulated fluence. Thus, as used in this specification, the term "target" or "target region" may refer to an entire region that is desired to be treated or a subset of such region. Similarly, as used in this specification, the term "critical organ" (aka "critical region") may refer to an entire region that contains healthy tissue desired to be protected or a subset of such region.

In the above embodiments, the method 200 involves a prediction of a target's movement. In other embodiments, the method 200 may not require a prediction of movement. For example, in other embodiments, the method 200 may use the current actual position of the target T and the current actual position of the critical organ C to determine a future target fluence to be applied. In such cases, when the radiation is actually applied to attempt to achieve the determined target fluence, the target T and the critical organ C may have already moved to different positions, thereby resulting in some inaccuracy of applied dose (e.g., more dose to the critical region C, not enough dose to the target T, too much dose to the target T, etc.). Such tracking error, for example, may be due to the processor's 54 processing delay to determine the target fluence and/or a delay by the machine to accomplish a machine configuration to carry out the prescribed target fluence. However, such tracking error can be addressed using the above described technique—e.g., by using the actual accumulated dose at the target T and the actual accumulated dose at the critical organ C (either or both of which may include dose error due to tracking error) to determine the next target fluence. Thus, the above method 200 may still provide a desirable treatment even if no prediction of movement is involved.

Further, in other embodiments, instead of determining treatment parameter(s) in real time during a treatment session, the above technique may be performed during a treatment planning. For example, an imaging system, e.g., a CT system, may first be used to determine a sequence of volumetric images (4D images) for different phases of a breathing cycle, and then for each breathing phase of a respiratory cycle, the target's T and critical region's C cumulated doses are determined (using the CT images) as a function of optimizable parameters, and the parameters are then optimized to determine the treatment plan. Any of the optimization algorithms known in the art may be used to perform the optimization during the planning phase. The optimization would be based on movement model, for example, from the 4D CT imaging and segmentation. In some embodiments, after a preliminary treatment plan has been determined, the treatment planning phase includes simulation of the treatment using the preliminary treatment plan and simulated movements of the patient. Such simulation may be implemented using features of the method 200 described herein. The simulation could contain a few modified movement patterns that are different from that derived from the 4D CT imaging. For examples, the modified movement pattern may be created by changing the breathing period, the speed at which the breathing phase changes, the amplitude of the breathing, and/or combination of the foregoing. During the simulation, hypothetical radiation is applied, and the accumulated doses at target T and critical region C are separately tracked as discussed. The treatment plan could then be modified based on the simulation. For example, if some region of the spinal cord is likely to get too much dose due to different movements and that is not allowed due to clinical reasons, the treatment plan could be reoptimized using different constraints in that region of spinal cord, or looser constraint could be used in target near that region. In some embodiments, different simulated movement patterns may be applied for different simulation sessions to confirm that the system for performing the actual real-time treatment planning can provide a desired radiation delivery under different movement scenarios.

Computer System Architecture

Figure 8:
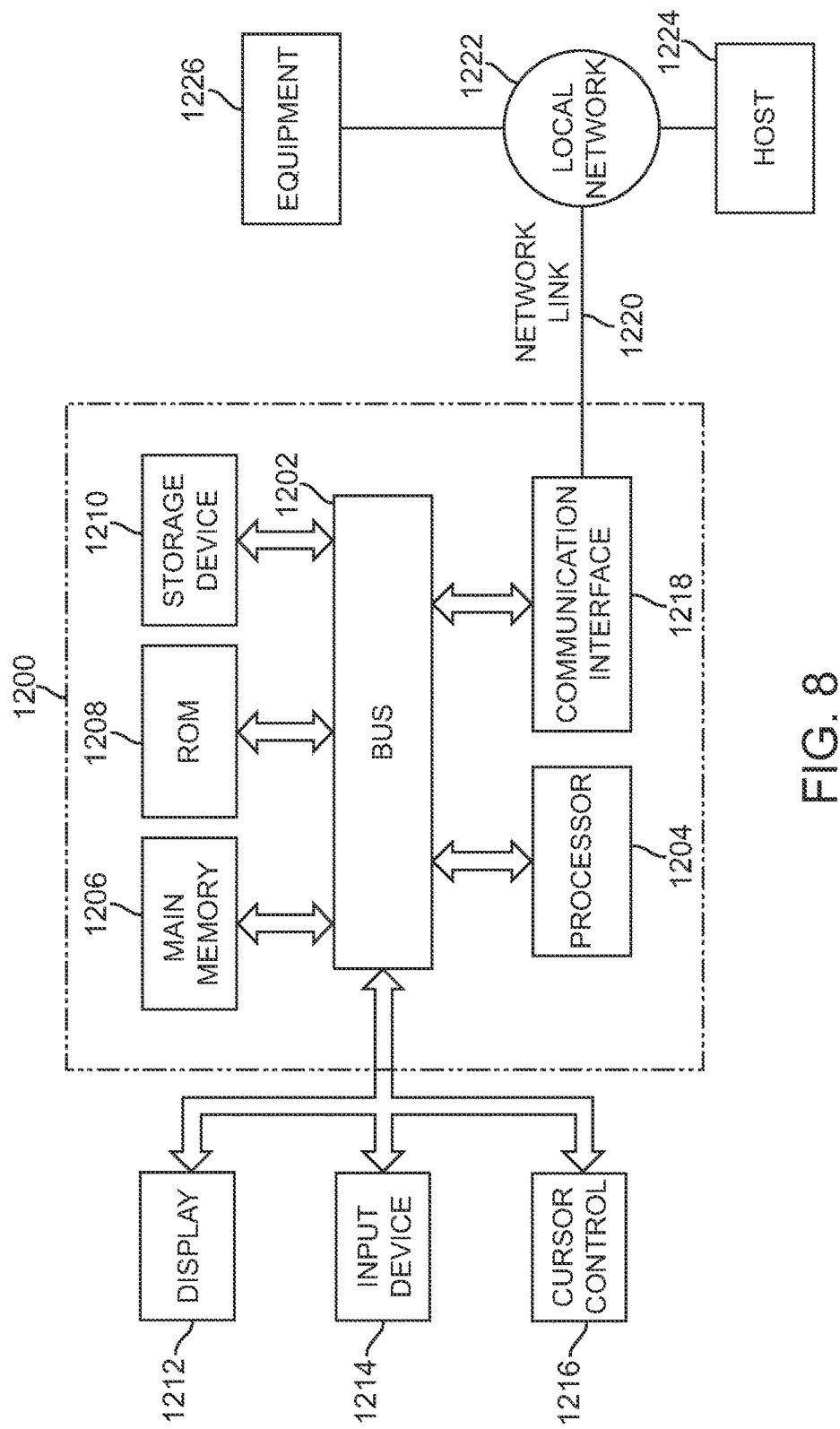
FIG. 8 is a block diagram of a computer system architecture, with which embodiments described herein may be implemented.

FIG. 8 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A medical method, comprising:
   determining a first two-dimensional fluence for a target region that is resulted at least in part from a previous radiation delivery;
   determining a second two-dimensional fluence for a critical region that is different from the target region;
   predicting a future position of the target region;
   predicting a future position of the critical region; and
   using the predicted future position of the target region and the predicted future position of the critical region, by a processor, to determine a target fluence so that when radiation is delivered at a future time based on the determined target fluence, the first two-dimensional fluence will be increased, wherein the target fluence represents a desired amount of fluence;
   wherein the method further comprises predicting an additional future position of the target region, and predicting an additional future position of the critical region.

2. The method of claim 1, further comprising translating the target fluence into machine parameter(s).

3. The method of claim 2, wherein the machine parameter(s) comprises a gantry angle, a gantry rotational speed, beam energy, radiation source angle(s), a dose rate, or a patient support's position.

4. The method of claim 2, wherein the target fluence is translated by the processor into the machine parameter(s) in real time.

5. The method of claim 1, further comprising translating the target fluence into a leaf sequence.

6. The method of claim 1, wherein the target fluence is determined by the processor in real time.

7. The method of claim 1, further comprising generating one or more control signal(s) to operate a treatment system based on the determined target fluence.

8. The method of claim 7, wherein the one or more control signal(s) is generated to operate the treatment system in an attempt to produce a target fluence that matches the determined target fluence.

9. The method of claim 8, wherein the produced target fluence is different from the determined target fluence.

10. The method of claim 7, further comprising determining actual position of the target region and actual position of the critical region when the radiation is applied, the radiation being applied based on the one or more control signal(s).

11. The method of claim 10, further comprising:
    updating the first two-dimensional fluence for the target region based on the actual position of the target region; and
    updating the second two-dimensional fluence for the critical region based on the actual position of the critical region.

12. The method of claim 1, wherein the target fluence is determined by the processor so that when the radiation is delivered at the future time based on the determined target fluence, the second two-dimensional fluence for the critical region will remain below a prescribed threshold for the critical region.

13. The method of claim 1, wherein the target fluence is determined by the processor so that when the radiation is delivered at a future time based on the determined target fluence, the first two-dimensional fluence will be increased to a value that is below a prescribed threshold for the target region.

14. An apparatus for determining a target fluence comprising a processor, wherein the processor is configured for:
    determining a first two-dimensional fluence for a target region that is resulted at least in part from a previous radiation delivery;
    determining a second two-dimensional fluence for a critical region that is different from the target region;
    predicting a future position of the target region;
    predicting a future position of the critical region; and
    using the predicted future position of the target region and the predicted future position of the critical region, by a processor, to determine a target fluence so that when radiation is delivered at a future time based on the determined target fluence, the first two-dimensional fluence will be increased, wherein the target fluence represents a desired amount of fluence;
    wherein the processor is configured to predict an additional future position of the target region, and predict an additional future position of the critical region.

15. The apparatus of claim 14, wherein the processor is further configured to translate the target fluence into machine parameter(s).

16. The apparatus of claim 15, wherein the machine parameter(s) comprises a gantry angle, a gantry rotational speed, beam energy, radiation source angle(s), a dose rate, or a patient support's position.

17. The apparatus of claim 15, wherein the processor is configured to translate the target fluence into the machine parameter(s) in real time.

18. The apparatus of claim 14, wherein the processor is configured to translate the target fluence into a leaf sequence.

19. The apparatus of claim 14, wherein the processor is configured to determine the target fluence in real time.

20. The apparatus of claim 14, wherein the processor is also configured to generate one or more control signal(s) to operate a treatment system based on the determined target fluence.

21. The apparatus of claim 20, wherein the one or more control signal(s) is for operating the treatment system in an attempt to produce a target fluence that matches the determined target fluence.

22. The apparatus of claim 21, wherein the produced target fluence is different from the determined target fluence.

23. The apparatus of claim 20, wherein the processor is configured to determine actual position of the target region and actual position of the critical region when the radiation is applied, the radiation being applied based on the one or more control signal(s).

24. The apparatus of claim 23, wherein the processor is also configured to:
update the first two-dimensional fluence for the target region based on the actual position of the target region; and
update the second two-dimensional fluence for the critical region based on the actual position of the critical region.

25. The apparatus of claim 14, wherein the processor is configured to determine the target fluence so that when the radiation is delivered at the future time based on the determined target fluence, the second two-dimensional fluence for the critical region will remain below a prescribed threshold for the critical region.

26. The apparatus of claim 14, wherein the processor is configured to determine the target fluence so that when the radiation is delivered at a future time based on the determined target fluence, the first two-dimensional fluence will be increased to a value that is below a prescribed threshold for the target region.

27. A medical method, comprising:
determining a first two-dimensional fluence for a target region that is resulted at least in part from a previous radiation delivery;
determining a second two-dimensional fluence for a critical region that is different from the target region;
predicting a future position of the target region;
predicting a future position of the critical region; and
using the predicted future position of the target region and the predicted future position of the critical region, by a processor, to determine a target fluence so that when radiation is delivered at a future time based on the determined target fluence, the first two-dimensional fluence will be increased, wherein the target fluence represents a desired amount of fluence;
wherein the future position of the target region, and the future position of the critical region, are separately predicted.

28. An apparatus for determining a target fluence comprising a processor, wherein the processor is configured for:
determining a first two-dimensional fluence for a target region that is resulted at least in part from a previous radiation delivery;
determining a second two-dimensional fluence for a critical region that is different from the target region;
predicting a future position of the target region;
predicting a future position of the critical region; and
using the predicted future position of the target region and the predicted future position of the critical region, by a processor, to determine a target fluence so that when radiation is delivered at a future time based on the determined target fluence, the first two-dimensional fluence will be increased, wherein the target fluence represents a desired amount of fluence;
wherein the processor is configured for separately predicting a future position of the target region, and predicting a future position of the critical region.

29. The medical method of claim 1, further comprising using the additional predicted future position of the target region, and the additional predicted future position of the critical region, by the processor, to determine an additional target fluence.

30. The apparatus of claim 14, wherein the processor is also configured to use the additional predicted future position of the target region, and the additional predicted future position of the critical region, to determine an additional target fluence.

* * * * *